US009440198B2

(12) United States Patent
McCloskey et al.

(10) Patent No.: US 9,440,198 B2
(45) Date of Patent: Sep. 13, 2016

(54) ZWITTERION-FUNCTIONALIZED BLOCK COPOLYMER MEMBRANES AND ASSOCIATED BLOCK COPOLYMER COMPOSITION

(71) Applicant: General Electric Company, Schenectady, NY (US)

(72) Inventors: Patrick Joseph McCloskey, Watervliet, NY (US); Julia Lam Lee, Niskayuna, NY (US); Hongyi Zhou, Niskayuna, NY (US); Cathryn Ellen Olsen, Wilton, NY (US); David Roger Moore, Rexford, NY (US); Matthew Jeremiah Misner, Delanson, NY (US); Louisa Ruth Carr, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 216 days.

(21) Appl. No.: 14/279,377

(22) Filed: May 16, 2014

(65) Prior Publication Data
US 2015/0328597 A1 Nov. 19, 2015

(51) Int. Cl.
| | |
|---|---|
| *B01D 71/80* | (2006.01) |
| *B01D 71/82* | (2006.01) |
| *B01D 71/40* | (2006.01) |
| *B01D 71/68* | (2006.01) |
| *B01D 69/08* | (2006.01) |
| *C08L 81/06* | (2006.01) |
| *A61M 1/16* | (2006.01) |

(52) U.S. Cl.
CPC .............. *B01D 71/80* (2013.01); *B01D 69/08* (2013.01); *B01D 71/82* (2013.01); *C08L 81/06* (2013.01); *A61M 1/16* (2013.01); *B01D 71/40* (2013.01); *B01D 71/68* (2013.01); *B01D 2323/36* (2013.01); *B01D 2325/18* (2013.01)

(58) Field of Classification Search
None
See application file for complete search history.

(56) References Cited

U.S. PATENT DOCUMENTS

| | | | |
|---|---|---|---|
| 6,852,816 B2 | 2/2005 | Lewis et al. | |
| 6,926,832 B2 | 8/2005 | Collins et al. | |
| 7,300,990 B2 | 11/2007 | Lewis et al. | |
| 7,985,339 B2 | 7/2011 | Zhang et al. | |
| 8,062,751 B2 | 11/2011 | Chang et al. | |
| 8,632,838 B2 | 1/2014 | Roth et al. | |
| 2008/0312349 A1 | 12/2008 | Yeager et al. | |
| 2011/0240550 A1 | 10/2011 | Moore et al. | |

(Continued)

FOREIGN PATENT DOCUMENTS

| | | |
|---|---|---|
| CN | 101003003 A | 7/2007 |
| CN | 102755844 A | 10/2012 |

(Continued)

OTHER PUBLICATIONS

PCT Search Report and Written Opinion issued in connection with corresponding PCT Application No. PCT/EP2015/060506 dated Jul. 17, 2015.

(Continued)

*Primary Examiner* — Krishnan S Menon
(74) *Attorney, Agent, or Firm* — John P. Darling

(57) ABSTRACT

A membrane including a block copolymer is presented. The block copolymer includes at least one block A including structural units having a formula (I), and at least one block B including structural units having a formula (II). A hollow-fiber membrane for hemodialysis or hemofiltration, and associated block copolymer are also presented.

18 Claims, 4 Drawing Sheets

(56) References Cited

U.S. PATENT DOCUMENTS

2012/0048799 A1  3/2012  Na et al.
2015/0136676 A1*  5/2015  Helm .................. C02F 1/445
                                                      210/232

FOREIGN PATENT DOCUMENTS

| JP | 2002030125 A | 1/2002 | |
|---|---|---|---|
| WO | 2011088505 A1 | 7/2011 | |
| WO | 2011156590 A2 | 12/2011 | |
| WO | WO 2015070004 A1 * | 5/2015 | ............. B01D 71/76 |

OTHER PUBLICATIONS

Sun et al., "Improved antifouling property of zwitterionic ultrafiltration membrane composed of acrylonitrile and sulfobetaine copolymer", Journal of Membrane Science, ScienceDirect, Nov. 15, 2006, pp. 299-305, vol. 285, Issues 1-2.

Yang et al., "Surface hydrophilization of microporous polypropylene membrane by grafting zwitterionic polymer for anti-biofouling", Journal of Membrane Science, ScienceDirect, Oct. 15, 2010, pp. 255-264, vol. 362, Issues 1-2.

* cited by examiner

ZWITTERION-FUNCTIONALIZED BLOCK COPOLYMER MEMBRANES AND ASSOCIATED BLOCK COPOLYMER COMPOSITION

BACKGROUND

The invention generally relates to block copolymer membranes. More particularly, the invention relates to zwitterion-functionalized block copolymer membranes.

Porous polymeric membranes, either in hollow fiber or flat sheet configurations may be employed in many applications, such as, hemodialysis, ultrafiltration, nanofiltration, reverse osmosis, gas separation, microfiltration, and pervaporation. For many of these applications, membranes with optimal selectivity as well as chemical, thermal and mechanical stability are desirable. In many applications (for example, bio-separation or water filtration) it may also be desirable to have membranes with one or more of improved hydrophilicity, improved biocompatibility, or low fouling.

Polyarylene ethers, in particular, polyethersulfones and polysulfones are often used as membrane materials because of their mechanical, thermal, and chemical stability. However, these polymers may not have the optimal biocompatibility and hydrophilicity for many applications. Further improvements in membrane hydrophilicity have been achieved by polymer blending, for example, fabricating the porous membrane in the presence of small amounts of hydrophilic polymers such as polyvinylpyrollidone (PVP). However, since PVP is water-soluble it is slowly leached from the porous polymer matrix creating product variability. Alternatively, hydrophilicity has been achieved via functionalization of the polymer backbone and introduction of carboxyl, nitrile or polyethylene glycol functionality, which may also provide chemical resistance and good mechanical properties. However, these chemical modifications may be complicated, expensive and inefficient.

Thus, porous membranes having one or both of optimal hydrophilicity and biocompatibility are desired. Further, polymers capable of being fabricated into hydrophilic porous membranes polymers are also desired.

BRIEF DESCRIPTION OF THE INVENTION

Embodiments of the present invention are included to meet these and other needs. One embodiment is a membrane including a block copolymer. The block copolymer includes at least one block A including structural units having a formula (I), and at least one block B including structural units having a formula (II):

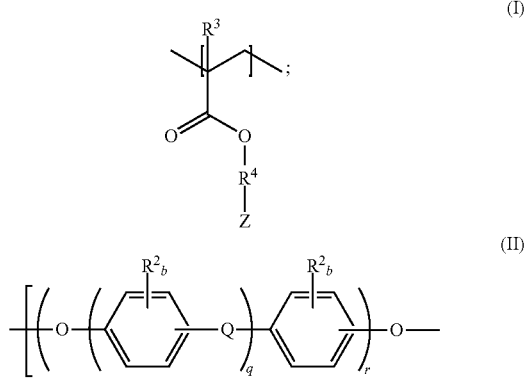

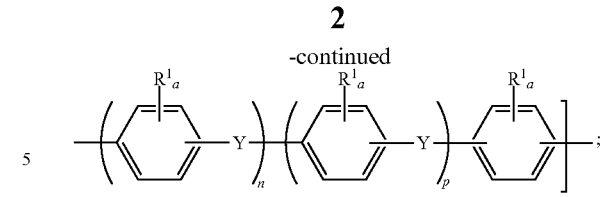

wherein "a" and "b" are independently at each occurrence 0, 1, 2, 3, or 4;

"n", "p", "q" and "r" are independently 0 or 1;

$R^1$ and $R^2$ are independently at each occurrence a hydrogen atom, a halogen atom, a nitro group, a $C_1$-$C_{12}$ aliphatic radical, a $C_3$-$C_{12}$ cycloaliphatic radical, or a $C_3$-$C_{12}$ aromatic radical;

$R^3$ is a hydrogen atom, a $C_1$-$C_{12}$ aliphatic radical, a $C_3$-$C_{12}$ cycloaliphatic radical, or a $C_3$-$C_{12}$ aromatic radical;

$R^4$ is a $C_1$-$C_{12}$ aliphatic radical, a $C_3$-$C_{12}$ cycloaliphatic radical, or a $C_3$-$C_{12}$ aromatic radical;

Y is independently at each occurrence a bond, an oxygen atom, a sulfur atom, a sulfinyl group, a sulfonyl group, a phenylphosphine group, a $C_1$-$C_{12}$ aliphatic radical, a $C_3$-$C_{12}$ cycloaliphatic radical, or a $C_3$-$C_{12}$ aromatic radical;

Q is a bond, an oxygen atom, a sulfur atom, a $C_1$-$C_{12}$ aliphatic radical, a $C_3$-$C_{12}$ cycloaliphatic radical, or a $C_3$-$C_{12}$ aromatic radical; and Z is a zwitterion functional group.

One embodiment is a hollow-fiber membrane for bio-separation. The membrane includes a block copolymer. The block copolymer includes at least one block A including structural units having a formula (I), and at least one block B including structural units having a formula (II):

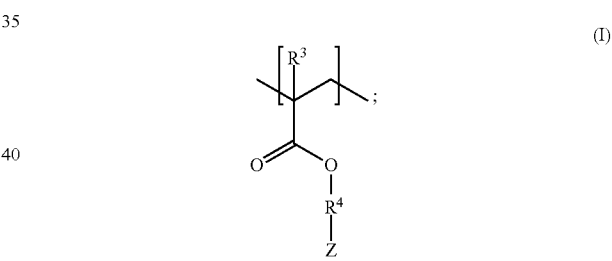

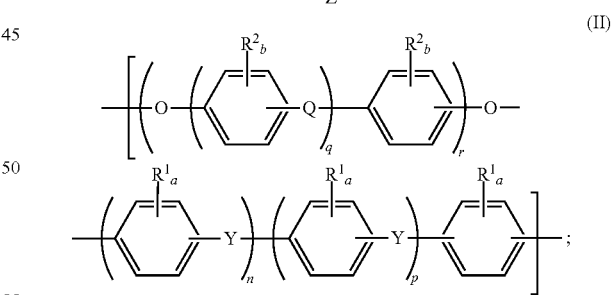

wherein "a" and "b" are independently at each occurrence 0, 1, 2, 3, or 4;

"n", "p", "q" and "r" are independently 0 or 1;

$R^1$ and $R^2$ are independently at each occurrence a hydrogen atom, a halogen atom, a nitro group, a $C_1$-$C_{12}$ aliphatic radical, a $C_3$-$C_{12}$ cycloaliphatic radical, or a $C_3$-$C_{12}$ aromatic radical;

$R^3$ is a hydrogen atom, a $C_1$-$C_{12}$ aliphatic radical, a $C_3$-$C_{12}$ cycloaliphatic radical, or a $C_3$-$C_{12}$ aromatic radical;

$R^4$ is a $C_1$-$C_{12}$ aliphatic radical, a $C_3$-$C_{12}$ cycloaliphatic radical, or a $C_3$-$C_{12}$ aromatic radical;

Y is independently at each occurrence a bond, an oxygen atom, a sulfur atom, a sulfinyl group, a sulfonyl group, a phenylphosphine group, a $C_1$-$C_{12}$ aliphatic radical, a $C_3$-$C_{12}$ cycloaliphatic radical, or a $C_3$-$C_{12}$ aromatic radical;
Q is a bond, an oxygen atom, a sulfur atom, a $C_1$-$C_{12}$ aliphatic radical, a $C_3$-$C_{12}$ cycloaliphatic radical, or a $C_3$-$C_{12}$ aromatic radical; and
Z is a zwitterion functional group.

One embodiment is a block copolymer including at least one block A including structural units having a formula (I), and at least one block B including structural units having a formula (II):

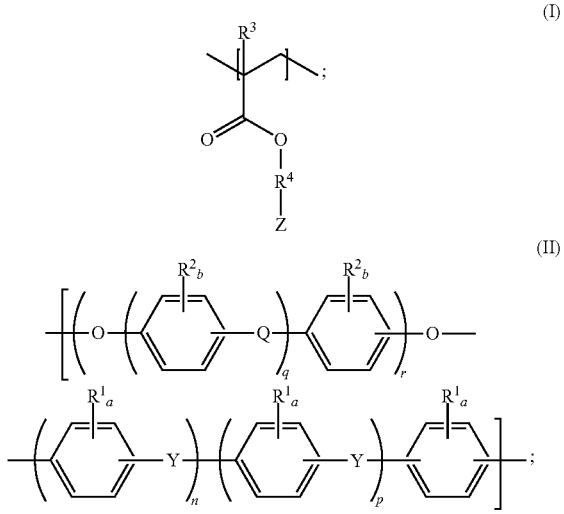

wherein "a" and "b" are independently at each occurrence 0, 1, 2, 3, or 4;
"n", "p", "q" and "r" are independently 0 or 1;
$R^1$ and $R^2$ are independently at each occurrence a hydrogen atom, a halogen atom, a nitro group, a $C_1$-$C_{12}$ aliphatic radical, a $C_3$-$C_{12}$ cycloaliphatic radical, or a $C_3$-$C_{12}$ aromatic radical;
$R^3$ is a hydrogen atom, a $C_1$-$C_{12}$ aliphatic radical, a $C_3$-$C_{12}$ cycloaliphatic radical, or a $C_3$-$C_{12}$ aromatic radical;
$R^4$ is a $C_1$-$C_{12}$ aliphatic radical, a $C_3$-$C_{12}$ cycloaliphatic radical, or a $C_3$-$C_{12}$ aromatic radical;
Y is independently at each occurrence a bond, an oxygen atom, a sulfur atom, a sulfinyl group, a sulfonyl group, a phenylphosphine group, a $C_1$-$C_{12}$ aliphatic radical, a $C_3$-$C_{12}$ cycloaliphatic radical, or a $C_3$-$C_{12}$ aromatic radical;
Q is a bond, an oxygen atom, a sulfur atom, a $C_1$-$C_{12}$ aliphatic radical, a $C_3$-$C_{12}$ cycloaliphatic radical, or a $C_3$-$C_{12}$ aromatic radical; and
Z is a zwitterion functional group.

DRAWINGS

These and other features, aspects, and advantages of the present invention will become better understood when the following detailed description is read with reference to the accompanying drawings, wherein.

DETAILED DESCRIPTION

Figure 1:
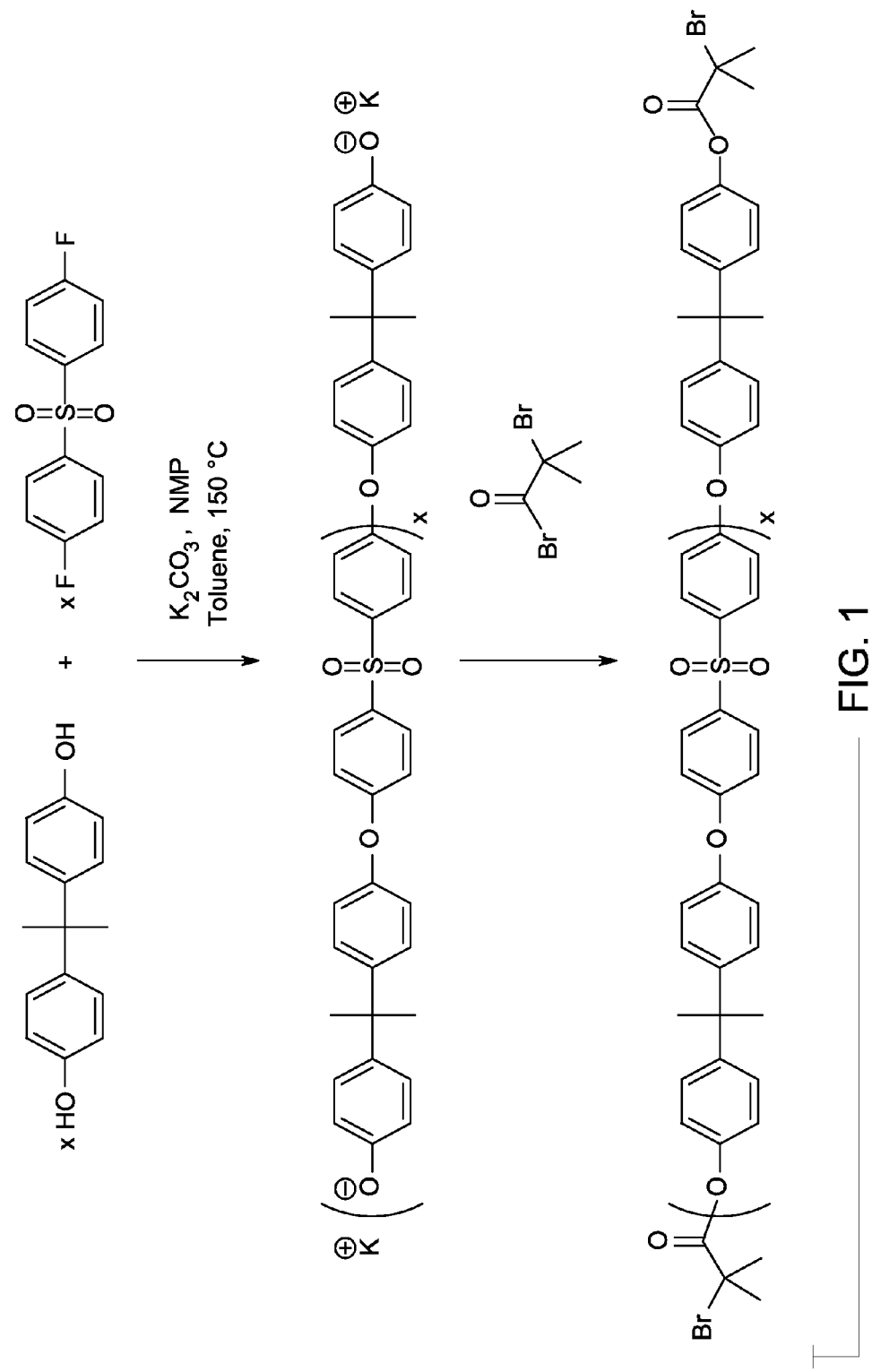
FIG. 1 shows the synthesis scheme for the macroinitiator, in accordance with some embodiments of the invention.

As discussed in detail below, some of the embodiments of the invention include block copolymer membranes including zwitterion functional groups. More particularly, embodiments of the invention relate to block copolymer hollow-fiber membranes used for one or more of bio-separation, water filtration, or hemodialysis.

Approximating language, as used herein throughout the specification and claims, may be applied to modify any quantitative representation that could permissibly vary without resulting in a change in the basic function to which it is related. Accordingly, a value modified by a term or terms, such as "about", and "substantially" is not to be limited to the precise value specified. In some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

In the following specification and the claims, the singular forms "a", "an" and "the" include plural referents unless the context clearly dictates otherwise. As used herein, the term "or" is not meant to be exclusive and refers to at least one of the referenced components being present and includes instances in which a combination of the referenced components may be present, unless the context clearly dictates otherwise.

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthraceneyl groups (n=3) and the like. The aromatic radical may also include nonaromatic components. For example, a benzyl group is an aromatic radical, which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., —OPhC$(CF_3)_2$PhO—), 4-chloromethylphen-1-yl, 3-trifluorovinyl-2-thienyl, 3-trichloromethylphen-1-yl (i.e., 3-CCl$_3$Ph-), 4-(3-bromoprop-1-yl)phen-1-yl (i.e., 4-BrCH$_2$CH$_2$CH$_2$Ph-), and the like. Further examples of aromatic radicals include 4-allyloxyphen-1-oxy, 4-aminophen-1-yl (i.e., 4-H$_2$NPh-), 3-aminocarbonylphen-1-yl (i.e., NH$_2$COPh-), 4-benzoylphen-1-yl, dicyanomethylidenebis(4-phen-1-yloxy) (i.e., —OPhC(CN)$_2$PhO—), 3-methylphen-1-yl, methylenebis(4-phen-1-yloxy) (i.e., —OPhCH$_2$PhO—), 2-ethylphen-1-yl, phenylethenyl, 3-formyl-2-thienyl, 2-hexyl-5-furanyl, hexamethylene-1,6-bis(4-phen-1-yloxy) (i.e., —OPh$(CH_2)_6$PhO—), 4-hydroxymethylphen-1-yl (i.e., 4-HOCH$_2$Ph-), 4-mercaptomethylphen-1-yl (i.e., 4-HSCH$_2$Ph-), 4-methylthiophen-1-yl (i.e., 4-CH$_3$SPh-), 3-methoxyphen-1-yl, 2-methoxycarbonylphen-1-yloxy (e.g., methyl salicyl), 2-nitromethylphen-1-yl (i.e., 2-NO$_2$CH$_2$Ph), 3-trimethylsilylphenl-1-yl, 4-t-butyldimethylsilylphenl-1-yl, 4-vinylphen-1-yl, vinylidenebis(phenyl), and the like. The term "a $C_3$-$C_{10}$ aromatic radical" includes aromatic radicals containing at least three but no more than 10 carbon atoms. The aromatic radical 1-imidazolyl ($C_3H_2N_2$—) represents a $C_3$ aromatic radical. The benzyl radical ($C_7H_7$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is a cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms, which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene-2,2-bis(cyclohex-4-yl) (i.e., —C$_6$H$_{10}$C(CF$_3$)$_2$C$_6$H$_{10}$—), 2-chloromethylcyclohex-1-yl, 3-difluoromethylenecyclohex-1-yl, 4-trichloromethylcyclohex-1-yloxy, 4-bromodichloromethylcyclohex-1-ylthio, 2-bromoethylcyclopent-1-yl, 2-bromopropylcyclohex-1-yloxy (e.g., CH$_3$CHBrCH$_2$C$_6$H$_{10}$O—), and the like. Further examples of cycloaliphatic radicals include 4-allyloxycyclohex-1-yl, 4-aminocyclohex-1-yl (i.e., H$_2$NC$_6$H$_{10}$—), 4-aminocarbonylcyclopent-1-yl (i.e., NH$_2$COC$_5$H$_8$—), 4-acetyloxycyclohex-1-yl, 2,2-dicyanoisopropylidenebis(cyclohex-4-yloxy) (i.e., —OC$_6$H$_{10}$C(CN)$_2$C$_6$H$_{10}$O—), 3-methylcyclohex-1-yl, methylenebis(cyclohex-4-yloxy) (i.e., —OC$_6$H$_{10}$CH$_2$C$_6$H$_{10}$O—), 1-ethylcyclobut-1-yl, cyclopropylethenyl, 3-formyl-2-terahydrofuranyl, 2-hexyl-5-tetrahydrofuranyl, hexamethylene-1,6-bis(cyclohex-4-yloxy) (i.e., —OC$_6$H$_{10}$(CH$_2$)$_6$C$_6$H$_{10}$O—), 4-hydroxymethylcyclohex-1-yl (i.e., 4-HOCH$_2$C$_6$H$_{10}$—), 4-mercaptomethylcyclohex-1-yl (i.e., 4-HSCH$_2$C$_6$H$_{10}$—), 4-methylthiocyclohex-1-yl (i.e., 4-CH$_3$SC$_6$H$_{10}$—), 4-methoxycyclohex-1-yl, 2-methoxycarbonylcyclohex-1-yloxy (2-CH$_3$OCOC$_6$H$_{10}$O—), 4-nitromethylcyclohex-1-yl (i.e., NO$_2$CH$_2$C$_6$H$_{10}$—), 3-trimethylsilylcyclohex-1-yl, 2-t-butyldimethylsilylcyclopent-1-yl, 4-trimethoxysilylethylcyclohex-1-yl (e.g., (CH$_3$O)$_3$SiCH$_2$CH$_2$C$_6$H$_{10}$—), 4-vinylcyclohexen-1-yl, vinylidenebis(cyclohexyl), and the like. The term "a $C_3$-$C_{10}$ cycloaliphatic radical" includes cycloaliphatic radicals containing at least three but no more than 10 carbon atoms. The cycloaliphatic radical 2-tetrahydrofuranyl ($C_4H_7O$—) represents a $C_4$ cycloaliphatic radical. The cyclohexylmethyl radical ($C_6H_{11}CH_2$—) represents a $C_7$ cycloaliphatic radical.

As used herein the term "aliphatic radical" refers to an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g., —CH$_2$CHBrCH$_2$—), and the like. Further examples of aliphatic radicals include allyl, aminocarbonyl (i.e., —CONH$_2$), carbonyl, 2,2-dicyanoisopropylidene (i.e., —CH$_2$C(CN)$_2$CH$_2$—), methyl (i.e., —CH$_3$), methylene (i.e., —CH$_2$—), ethyl, ethylene, formyl (i.e., —CHO), hexyl, hexamethylene, hydroxymethyl (i.e., —CH$_2$OH), mercaptomethyl (i.e., —CH$_2$SH), methylthio (i.e., —SCH$_3$), methylthiomethyl (i.e., —CH$_2$SCH$_3$), methoxy, methoxycarbonyl (i.e., CH$_3$OCO—), nitromethyl (i.e., —CH$_2$NO$_2$), thiocarbonyl, trimethylsilyl (i.e., (CH$_3$)$_3$Si—), t-butyldimethylsilyl, 3-trimethyoxysilylpropyl (i.e., (CH$_3$O)$_3$SiCH$_2$CH$_2$CH$_2$—), vinyl, vinylidene, and the like. By way of further example, a $C_1$-$C_{10}$ aliphatic radical contains at least one but no more than 10 carbon atoms. A methyl group (i.e., CH$_3$—) is an example of a C$_1$ aliphatic radical. A decyl group (i.e., CH$_3$(CH$_2$)$_9$—) is an example of a C$_{10}$ aliphatic radical.

As discussed in detail below, some embodiments of the invention are directed to a membrane composed of a block copolymer. The term "block copolymer" as used herein refers to blocks of monomers of the same type that are arranged sequentially. For example, an AB block copolymer includes a block A formed from monomers of the same type; and a block B formed from monomers of the same type. The blocks A and B may have the same or different block length, that is, the number of repeat units in the two blocks may be the same or different. Similarly, an ABA block copolymer includes a block A formed from monomers of the same type; a block B formed from monomers of the same type, and another block A formed from monomers of the same type. In such instances, typically the two A blocks have the same number of repeating units. Further, the term "block copolymer" as used herein refers to the zwitterion-functionalized block copolymer, unless the context clearly indicates otherwise.

The block copolymer in accordance with one embodiment of the invention includes at least one block A including structural units having a formula (I), and at least one block B including structural units having a formula (II):

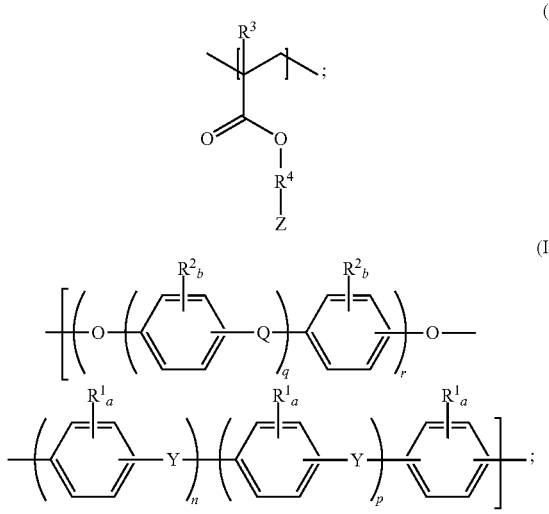

wherein "a" and "b" are independently at each occurrence 0, 1, 2, 3, or 4;

"n", "p", "q" and "r" are independently 0 or 1;

R$^1$ and R$^2$ are independently at each occurrence a hydrogen atom, a halogen atom, a nitro group, a C$_1$-C$_{12}$ aliphatic radical, a C$_3$-C$_{12}$ cycloaliphatic radical, or a C$_3$-C$_{12}$ aromatic radical;

R$^3$ is a hydrogen atom, a C$_1$-C$_{12}$ aliphatic radical, a C$_3$-C$_{12}$ cycloaliphatic radical, or a C$_3$-C$_{12}$ aromatic radical;

R$^4$ is a C$_1$-C$_{12}$ aliphatic radical, a C$_3$-C$_{12}$ cycloaliphatic radical, or a C$_3$-C$_{12}$ aromatic radical;

Y is independently at each occurrence a bond, an oxygen atom, a sulfur atom, a sulfinyl group, a sulfonyl group, a phenylphosphine group, a C$_1$-C$_{12}$ aliphatic radical, a C$_3$-C$_{12}$ cycloaliphatic radical, or a C$_3$-C$_{12}$ aromatic radical;

Q is a bond, an oxygen atom, a sulfur atom, a C$_1$-C$_{12}$ aliphatic radical, a C$_3$-C$_{12}$ cycloaliphatic radical, or a C$_3$-C$_{12}$ aromatic radical; and Z is a zwitterion functional group.

In some embodiments, the block B may include a suitable thermoplastic polymer including structural units having a formula (II). Non-limiting examples of suitable block B structural units include polysulfones, polyethersulfones, polyketones, polyetherketones, or polyetheretherketones. In some embodiments, the block B includes polysulfone or polyethersulfone structural units.

In some embodiments, the block B includes structural units having a formula (III):

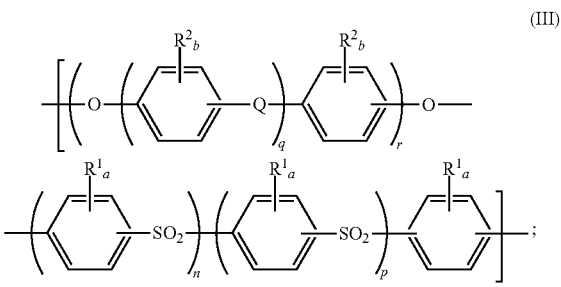

wherein "a" and "b" are independently at each occurrence 0, 1, 2, 3, or 4;

"n", "p", "q" and "r" are independently 0 or 1;

Q is a bond, an oxygen atom, a sulfur atom, a C$_1$-C$_{12}$ aliphatic radical, a C$_3$-C$_{12}$ cycloaliphatic radical, or a C$_3$-C$_{12}$ aromatic radical; and R$^1$ and R$^2$ are independently at each occurrence a hydrogen atom, a halogen atom, a nitro group, a C$_1$-C$_{12}$ aliphatic radical, a C$_3$-C$_{12}$ cycloaliphatic radical, or a C$_3$-C$_{12}$ aromatic radical.

In some embodiments, R$^1$ and R$^2$ are independently at each occurrence hydrogen, methyl, ethyl, propyl, isopropyl, butyl, hexyl, heptyl, octyl, 4-methylpent-1-yl, phenyl, naphthyl or biphenyl. In certain embodiments, R$^1$ and R$^2$ are independently at each occurrence a hydrogen atom. In some embodiments, Q is a C$_1$-C$_{12}$ aliphatic radical. In certain embodiments, Q is methyl, ethyl, propyl, isopropyl, butyl, hexyl, heptyl, octyl, 4-methylpent-1-yl, or phenyl.

In certain embodiments, the block B includes structural units having a formula (X):

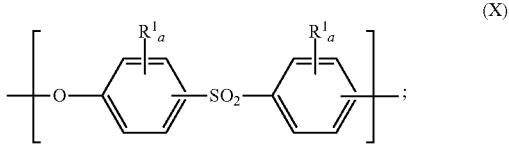

wherein "a" is independently at each occurrence 0, 1, 2, 3, or 4; and

R$^1$ is independently at each occurrence a hydrogen atom, a halogen atom, a nitro group, a C$_1$-C$_{12}$ aliphatic radical, a C$_3$-C$_{12}$ cycloaliphatic radical, or a C$_3$-C$_{12}$ aromatic radical.

In certain embodiments, the block B includes structural units having a formula (XI):

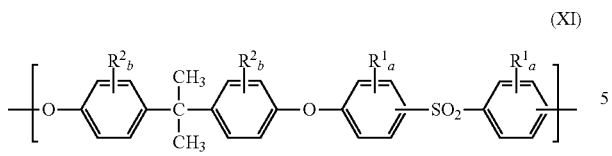

(XI)

wherein "a" and 'b' are independently at each occurrence 0, 1, 2, 3, or 4; and
$R^1$ and $R^2$ are independently at each occurrence a hydrogen atom, a halogen atom, a nitro group, a $C_1$-$C_{12}$ aliphatic radical, a $C_3$-$C_{12}$ cycloaliphatic radical, or a $C_3$-$C_{12}$ aromatic radical.

As noted earlier, the block copolymer further includes at least one block A including structural units having a formula (I):

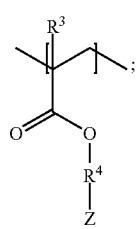

(I)

wherein $R^3$ is a hydrogen atom, a $C_1$-$C_{12}$ aliphatic radical, a $C_3$-$C_{12}$ cycloaliphatic radical, or a $C_3$-$C_{12}$ aromatic radical; $R^4$ is a $C_1$-$C_{12}$ aliphatic radical, a $C_3$-$C_{12}$ cycloaliphatic radical, or a $C_3$-$C_{12}$ aromatic radical; and
Z is a zwitterion functional group.

The term "zwitterion functional group" as used herein refers to a moiety including both positive and negatively charged groups in the same molecule. Without being bound by any theory, it is believed that the zwitterion functional groups may provide improved hydrophilicity and biocompatibility for the block copolymer while maintaining membrane-formation capability.

Non-limiting examples of suitable zwitterion functional group include sulfobetaine, carboxybetaine, phosphorylcholine, or combinations thereof. In certain embodiments, the block A includes structural units having a formula (IV):

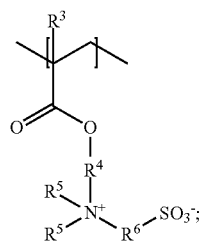

(IV)

wherein $R^3$ and $R^5$ are independently at each occurrence a hydrogen atom, a $C_1$-$C_{12}$ aliphatic radical, a $C_3$-$C_{12}$ cycloaliphatic radical, or a $C_3$-$C_{12}$ aromatic radical; and
$R^4$ and $R^6$ are independently a $C_1$-$C_{12}$ aliphatic radical, a $C_3$-$C_{12}$ cycloaliphatic radical, or a $C_3$-$C_{12}$ aromatic radical.

In certain embodiments, the block A includes structural units having a formula (XII):

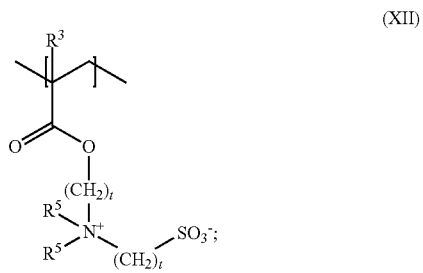

(XII)

wherein "t" is an integer in a range from about 1 to about 10; and
$R^3$ and $R^5$ are independently at each occurrence a hydrogen atom, a $C_1$-$C_{12}$ aliphatic radical, a $C_3$-$C_{12}$ cycloaliphatic radical, or a $C_3$-$C_{12}$ aromatic radical.

In some embodiments the block A may be entirely composed of structural units having the formula (I). In some other embodiments, the block A may further include structural units having a formula (V):

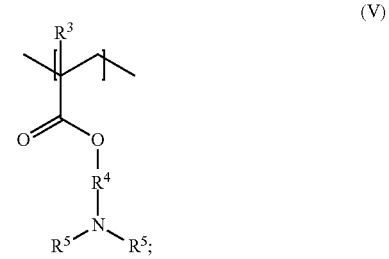

(V)

wherein $R^3$ and $R^5$ are independently at each occurrence a hydrogen atom, a $C_1$-$C_{12}$ aliphatic radical, a $C_3$-$C_{12}$ cycloaliphatic radical, or a $C_3$-$C_{12}$ aromatic radical; and $R^4$ is a $C_1$-$C_{12}$ aliphatic radical, a $C_3$-$C_{12}$ cycloaliphatic radical, or a $C_3$-$C_{12}$ aromatic radical.

In such embodiments, the block A may include sequential or random arrangement of the structural units having formulae (I) and (V). In certain embodiments, the block B includes random arrangement of the structural units having formulae (I) and (V). The number of structural units having formula (I) may depend in part on the mole fraction of zwitterion functional groups desired in the block A. In some embodiments, a mole fraction of the zwitterion functional groups in the block A is in a range from about 5 percent to about 100 percent. In some embodiments, a mole fraction of the zwitterion functional group in the block A is in a range from about 35 percent to about 70 percent.

The block copolymer may be further characterized by the number of repeat units in the blocks A and B. In some embodiments, the number of repeat units in the block B is in a range from about 20 to about 200. In some embodiments, the number of repeat units in the block B is in a range from about 30 to about 100. In some embodiments, the number of repeat units in the block B is in a range from about 50 to about 75. The term "repeat unit" as used herein in this context refers to structural units having a formula (II).

In some embodiments, the number of repeat units in the block A is in a range from about 1 to about 25. In some embodiments, the number of repeat units in the block A is in a range from about 2 to about 20. In some embodiments, the number of repeat units in the block A is in a range from about 3 to about 12. It should be noted that the term "repeat unit"

as used herein in this context refers to both structural units having a formula (I) and structural units having a formula (V), with the proviso that at least one repeat unit in the block A includes structural units having a formula (I).

The block copolymer may be an AB-type block copolymer or an ABA-type block copolymer. It should be noted that the term "AB-type block copolymer" as used herein refers to block copolymers having an A block and a B block. However, in such instances, the A block and the B block may be further connected to each other using a suitable linking group (for example, an initiator residue). As described in detail later, in some embodiments, the block copolymer may be formed by atom transfer radical polymerization (ATRP), and in such instances the blocks A and B may be linked by a linking group including an ATRP initiator residue. Similarly, the term "ABA-type block copolymer" has used herein refers to block copolymers having a first A block, a B block, and a second A block. The A and B blocks may be further connected to each other using a suitable linking group (for example, an initiator residue).

Non-limiting example of a suitable AB-type block copolymer includes structural units having a formula (VI):

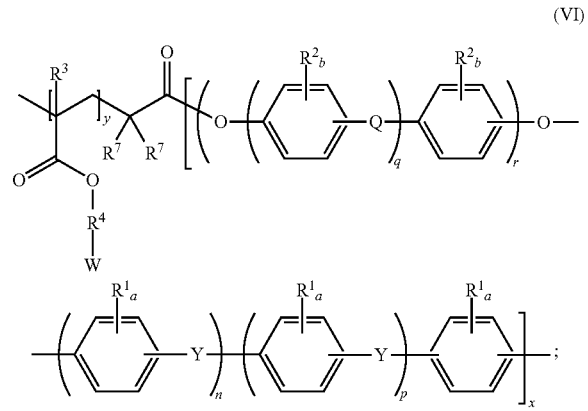

(VI)

wherein "a" and "b" are independently at each occurrence 0, 1, 2, 3, or 4;
"n", "p", "q" and "r" are independently 0 or 1;
"x" is an integer in a range from about 20 to about 200;
"y" is an integer in a range from about 1 to about 25;
Y is independently at each occurrence a bond, an oxygen atom, a sulfur atom, a sulfinyl group, a sulfonyl group, a phenylphosphine group, a $C_1$-$C_{12}$ aliphatic radical, a $C_3$-$C_{12}$ cycloaliphatic radical, or a $C_3$-$C_{12}$ aromatic radical;
Q is a bond, an oxygen atom, a sulfur atom, a $C_1$-$C_{12}$ aliphatic radical, a $C_3$-$C_{12}$ cycloaliphatic radical, or a $C_3$-$C_{12}$ aromatic radical;
W is independently at each occurrence a radical having a formula (VII) or (VIII):

(VII)

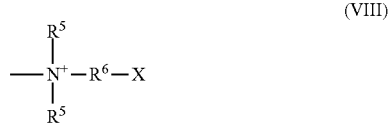

(VIII)

with the proviso that at least one of W in the block copolymer is a radical having the formula (VIII);
$R^1$ and $R^2$ are independently at each occurrence a hydrogen atom, a halogen atom, a nitro group, a $C_1$-$C_{12}$ aliphatic radical, a $C_3$-$C_{12}$ cycloaliphatic radical, or a $C_3$-$C_{12}$ aromatic radical;
$R^3$, $R^5$, and $R^7$ are independently at each occurrence a hydrogen atom, a $C_1$-$C_{12}$ aliphatic radical, a $C_3$-$C_{12}$ cycloaliphatic radical, or a $C_3$-$C_{12}$ aromatic radical; and
$R^4$ and $R^6$ are independently a $C_1$-$C_{12}$ aliphatic radical, a $C_3$-$C_{12}$ cycloaliphatic radical, or a $C_3$-$C_{12}$ aromatic radical.

Non-limiting example of a suitable ABA-type block copolymer includes structural units having a formula (IX):

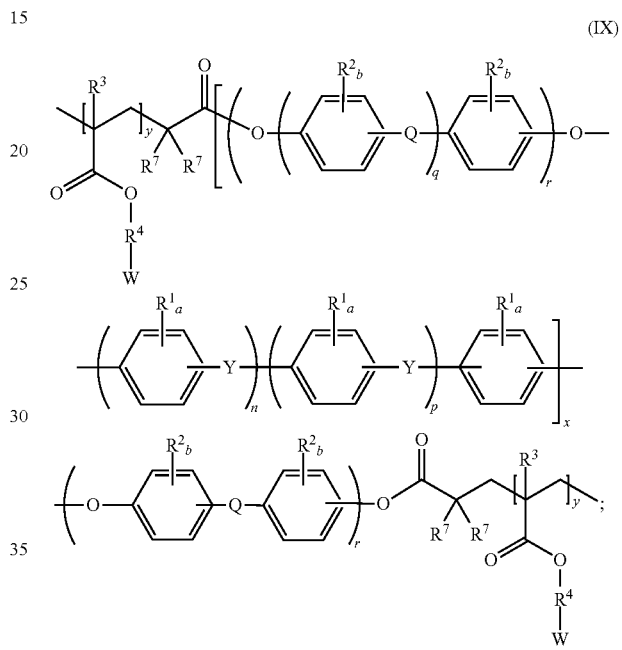

(IX)

wherein "a" and "b" are independently at each occurrence 0, 1, 2, 3, or 4;
"n", "p", "q" and "r" are independently 0 or 1;
"x" is an integer in a range from about 20 to about 200;
"y" is an integer in a range from about 1 to about 25;
Y is independently at each occurrence a bond, an oxygen atom, a sulfur atom, a sulfinyl group, a sulfonyl group, a phenylphosphine group, a $C_1$-$C_{12}$ aliphatic radical, a $C_3$-$C_{12}$ cycloaliphatic radical, or a $C_3$-$C_{12}$ aromatic radical;
Q is a bond, an oxygen atom, a sulfur atom, a $C_1$-$C_{12}$ aliphatic radical, a $C_3$-$C_{12}$ cycloaliphatic radical, or a $C_3$-$C_{12}$ aromatic radical;
W is independently at each occurrence a radical having a formula (VII) or (VIII):

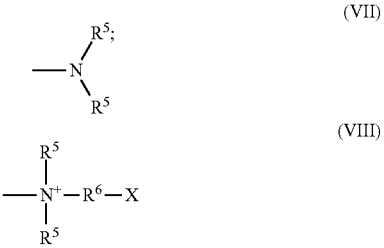

(VII)

(VIII)

with the proviso that at least one W in the block copolymer is a radical having the formula (VIII);

$R^1$ and $R^2$ are independently at each occurrence a hydrogen atom, a halogen atom, a nitro group, a $C_1$-$C_{12}$ aliphatic radical, a $C_3$-$C_{12}$ cycloaliphatic radical, or a $C_3$-$C_{12}$ aromatic radical;

$R^3$, $R^5$, and $R^7$ are independently at each occurrence a hydrogen atom, a $C_1$-$C_{12}$ aliphatic radical, a $C_3$-$C_{12}$ cycloaliphatic radical, or a $C_3$-$C_{12}$ aromatic radical; and $R^4$ and $R^6$ are independently a $C_1$-$C_{12}$ aliphatic radical, a $C_3$-$C_{12}$ cycloaliphatic radical, or a $C_3$-$C_{12}$ aromatic radical.

A block copolymer is also presented. The block copolymer includes at least one block A including structural units having a formula (I), and at least one block B including structural units having a formula (II), as described above. In some embodiments, the block copolymer is an AB-type block copolymer including structural units having a formula (VI). In some embodiments, the block copolymer is an ABA-type block copolymer including structural units having a formula (IX).

The block copolymers may be synthesized using any suitable techniques. In certain embodiments, the block copolymers may be synthesized by atom transfer radical polymerization (ATRP) of a macroinitiator (comprising block B) with a suitable acrylate monomer, followed by functionalizing the resulting polymer with zwitterion groups. The macroinitiator may be further synthesized by polycondensation of suitable monomers to form block B; and by end-capping the resulting polymer with an ATRP-active initiator.

The block B may be synthesized in some embodiments by reacting at least one aromatic dihydroxy compound with at least one aromatic dihalide compound. The reaction may be effected in a polar aprotic solvent in the presence of an alkali metal compound, and optionally, in the presence of catalysts.

Exemplary aromatic dihalide compounds that may be used include 4,4'-bis(chlorophenyl)sulfone, 2,4'-bis(chlorophenyl) sulfone, 2,4-bis(chlorophenyl) sulfone, 4,4'-bis(fluorophenyl)sulfone, 2,4'-bis(fluorophenyl)sulfone, 2,4-bis(fluorophenyl) sulfone, 4,4'-bis(chlorophenyl) sulfoxide, 2,4'-bis(chlorophenyl) sulfoxide, 2,4-bis(chlorophenyl) sulfoxide, 4,4'-bis(fluorophenyl)sulfoxide, 2,4'-bis(fluorophenyl)sulfoxide, 2,4-bis(fluorophenyl) sulfoxide, 4,4'-bis(fluorophenyl)ketone, 2,4'-bis(fluorophenyl)ketone, 2,4-bis(fluorophenyl)ketone, 1,3-bis(4-fluorobenzoyl)benzene, 1,4-bis(4-fluorobenzoyl)benzene, 4,4'-bis(4-chlorophenyl) phenylphosphine oxide, 4,4'-bis(4-fluorophenyl) phenylphosphine oxide, 4,4'-bis(4-fluorophenylsulfonyl)-1,1'-biphenyl, 4,4'-bis(4-chlorophenylsulfonyl)-1,1'-biphenyl, 4,4'-bis(4-fluorophenylsulfoxide)-1,1'-biphenyl, and 4,4'-bis(4-chlorophenylsulfoxide)-1,1'-biphenyl.

Non-limiting examples of suitable aromatic dihydroxy compounds that may be used include 4,4'-dihydroxyphenyl sulfone, 2,4'-dihydroxyphenyl sulfone, 4,4'-dihydroxyphenyl sulfoxide, 2,4'-dihydroxyphenyl sulfoxide, bis(3,5-dimethyl-4-hydroxyphenyl) sulfoxide, bis(3,5-dimethyl-4-hydroxyphenyl) sulfone, 4,4-(phenylphosphinyl)diphenol, 4,4'-oxydiphenol, 4,4'-thiodiphenol, 4,4'-dihydroxybenzophenone, 4,4'dihydroxyphenylmethane, hydroquinone, resorcinol, 5-cyano-1,3-dihydroxybenzene, 4-cyano-1,3,-dihydroxybenzene, 2-cyano-1,4-dihydroxybenzene, 2-methoxyhydroquinone, 2,2'-biphenol, 4,4'-biphenol, 2,2'-dimethylbiphenol 2,2',6,6'-tetramethylbiphenol, 2,2',3,3',6,6'-hexamethylbiphenol, 3,3',5,5'-tetrabromo-2,2'6,6'-tetramethylbiphenol, 4,4'-isopropylidenediphenol (bisphenol A), 4,4'-isopropylidenebis(2,6-dimethylphenol) (teramethylbisphenol A), 4,4'-isopropylidenebis(2-methylphenol), 4,4'-isopropylidenebis(2-allylphenol), 4,4'-isopropylidenebis(2-allyl-6-methylphenol), 4,4'(1,3-phenylenediisopropylidene) bisphenol (bisphenol M), 4,4'-isopropylidenebis(3-phenylphenol), 4,4'-isopropylidene-bis(2-phenylphenol), 4,4'-(1,4-phenylenediisoproylidene)bisphenol (bisphenol P), 4,4'-ethylidenediphenol (bisphenol E), 4,4'-oxydiphenol, 4,4'-thiodiphenol, 4,4'-thiobis(2,6-dimethylphenol), 4,4'-sulfonyldiphenol, 4,4'-sulfonylbis(2,6-dimethylphenol) 4,4'-sulfinyldiphenol, 4,4'-hexafluoroisoproylidene)bisphenol (Bisphenol AF), 4,4'-hexafluoroisoproylidene) bis(2,6-dimethylphenol), 4,4'-(1-phenylethylidene)bisphenol (Bisphenol AP), 4,4'-(1-phenylethylidene)bis(2,6-dimethylphenol), bis(4-hydroxyphenyl)-2,2-dichloroethylene (Bisphenol C), bis(4-hydroxyphenyl)methane (Bisphenol-F), bis(2,6-dimethyl-4-hydroxyphenyl)methane, 2,2-bis(4-hydroxyphenyl) butane, 3,3-bis(4-hydroxyphenyl)pentane, 4,4'-(cyclopentylidene)diphenol, 4,4'-(cyclohexylidene)diphenol (Bisphenol Z), 4,4'-(cyclohexylidene)bis(2-methylphenol), 4,4'-(cyclododecylidene)diphenol, 4,4'-(bicyclo[2.2.1]heptylidene)diphenol, 4,4'-(9H-fluorene-9,9-diyl)diphenol, 3,3'-bis(4-hydroxyphenyl)isobenzofuran-1 (3H)-one, 1-(4-hydroxyphenyl)-3,3'-dimethyl-2,3-dihydro-1H-inden-5-ol, 1-(4-hydroxy-3,5-dimethylphenyl)-1,3,3',4,6-pentamethyl-2,3-dihydro-1H-in-den-5-ol, 3,3,3',3'-tetramethyl-2,2',3,3'-tetrahydro-1,1'-spirobi[indene]-5,6'-diol (Spirobiindane), dihydroxybenzophenone (bisphenol K), thiodiphenol (Bisphenol S), bis(4-hydroxyphenyl)diphenyl methane, bis(4-hydroxyphenoxy)-4,4'-biphenyl, 4,4'-bis(4-hydroxyphenyl) diphenyl ether, 9,9-bis(3-methyl-4-hydroxyphenyl) fluorene, and N-phenyl-3,3-bis-(4-hydroxyphenyl)phthalimide.

A basic salt of an alkali metal compound may be used to effect the reaction between the dihalo and dihydroxy aromatic compounds. Exemplary compounds include alkali metal hydroxides, such as, but not limited to, lithium hydroxide, sodium hydroxide, potassium hydroxide, rubidium hydroxide, and cesium hydroxide; alkali metal carbonates, such as, but not limited to, lithium carbonate, sodium carbonate, potassium carbonate, rubidium carbonate, and cesium carbonate; and alkali metal hydrogen carbonates, such as but not limited to lithium hydrogen carbonate, sodium hydrogen carbonate, potassium hydrogen carbonate, rubidium hydrogen carbonate, and cesium hydrogen carbonate. Combinations of these compounds may also be used to effect the reaction.

Some examples of the aprotic polar solvent that may be used include N,N-dimethylformamide, N,N-diethylformamide, N,N-dimethylacetamide, N,N-diethylacetamide, N,N-dipropylacetamide, N,N-dimethylbenzamide, N-methyl-2-pyrrolidone (NMP), N-ethyl-2-pyrrolidone, N-isopropyl-2-pyrrolidone, N-isobutyl-2-pyrrolidone, N-n-propyl-2-pyrrolidone, N-n-butyl-2-pyrrolidone, N-cyclohexyl-2-pyrrolidone, N-methyl-3-methyl-2-pyrrolidone, N-ethyl-3-methyl-pyrrolidone, N-methyl-3,4,5-trimethyl-2-pyrrolidone, N-methyl-2-piperidone, N-ethyl-2-piperidone, N-isopropyl-2-piperidone, N-methyl-6-methyl-2-piperidone, N-methyl-3-ethylpiperidone, dimethylsulfoxide (DMSO), diethylsulfoxide, sulfolane, 1-methyl-1-oxosulfolane, 1-ethyl-1-oxosulfolane, 1-phenyl-1-oxosulfolane, N,N'-dimethylimidazolidinone (DMI), diphenylsulfone, and combinations thereof. The amount of solvent to be used is typically an amount that is sufficient to dissolve the dihalo and dihydroxy aromatic compounds.

The reaction may be conducted at a temperature in a range from about 100° C. to about 300° C. in some embodiments, from about 120° C. to about 200° C. in some embodiments, and from about 150° C. to about 200° C. in particular embodiments. The reaction mixture may be further dried by addition to the initial reaction mixture of, along with the polar aprotic solvent, a solvent that forms an azeotrope with water. Examples of such solvents include toluene, benzene, xylene, ethylbenzene and chlorobenzene. After removal of residual water by azeotropic drying, the reaction may be carried out at the elevated temperatures described above. The reaction is typically conducted for a time period ranging from about 1 hour to about 72 hours in some embodiments, and from about 1 hour to about 10 hours in particular embodiments.

After completion of the reaction, the polymer including block B may be separated from the inorganic salts, precipitated into a non-solvent and collected by filtration and drying. Examples of non-solvents include water, methanol, ethanol, propanol, butanol, acetone, methyl ethyl ketone, methyl isobutyl ketone, gamma.-butyrolactone, and combinations thereof.

The macroinitiator may be further synthesized by end-capping the resulting polymer with an ATRP-active end group. Non limiting examples of suitable end-groups include 2-bromoisobutyryl bromide (BiBB). The copolymer may be synthesized by copper-mediated polymerization of the macroinitiator with a suitable acrylate, for example, N,N-dimethylaminoethyl methacrylate, N,N-dimethylaminoethyl acrylate, or combinations thereof. The zwitterion functionalized block copolymer may be then synthesized by reacting the resulting copolymer with a suitable compound (for example, sultone) at elevated temperatures.

The glass transition temperature, $T_g$, of the block copolymer may be in a range from about 120° C. to about 280° C. in one embodiment, and may be in a range from about 140° C. to about 200° C. in another embodiment. The block copolymer may be further characterized by the number average molecular weight ($M_n$). In one embodiment, the $M_n$ of the block copolymer may be in the range from about 10,000 grams per mole (g/mol) to about 1,000,000 g/mol. In another embodiment, the $M_n$ may be in a range from about 15,000 g/mol to about 200,000 g/mol.

The block copolymer and the membrane including the block copolymer may be further characterized by its hydrophilicity. In some embodiments, the block copolymer has a contact angle with water less than about 80 degrees measured on a surface of the block copolymer cast as a film on a glass substrate. In some embodiments, the block copolymer has a contact angle with water less than about 50 degrees measured on a surface of the block copolymer cast as a film on a glass substrate. In particular embodiments, the block copolymer has a contact angle with water less than about 30 degrees measured on a surface of the block copolymer cast as a film on a glass substrate.

The membrane may have a hollow fiber configuration or a flat sheet configuration. In particular embodiments, the membrane may have a hollow fiber configuration. In some embodiments, a hollow fiber membrane composed of a block copolymer in accordance with embodiments of the invention, is presented. In some embodiments, a hollow-fiber membrane module including a plurality of hollow-fiber membranes is presented.

The membranes in accordance with embodiments of the invention may be made by processes known in the art. Suitable techniques include, but are not limited to: dry-phase separation membrane formation process; wet-phase separation membrane formation process; dry-wet phase separation membrane formation process; thermally-induced phase-separation membrane formation process. Further, post membrane-formation, the membrane may be subjected to a membrane conditioning process or a treatment process prior to its use in a separation application. Representative processes may include thermal annealing to relieve stresses or pre-equilibration in a solution similar to the feed stream the membrane will contact.

In one embodiment, the membranes may be prepared by phase inversion. The phase inversion process includes 1) vapor-induced phase separation (VIPS), also called "dry casting" or "air casting"; 2) liquid-induced phase separation (LIPS), mostly referred to as "immersion casting" or "wet casting"; and 3) thermally induced phase separation (TIPS), frequently called "melt casting". The phase inversion process can produce integrally skinned asymmetric membranes. In some embodiments, the membranes may be cross-linked to provide additional support.

The membrane may be designed and fabricated to have specific pore sizes so that solutes having sizes greater than the pore sizes may not be able to pass through. In one embodiment, the pore size may be in a range from about 0.5 nanometers to about 100 nanometers. In another embodiment, the pore size may be in a range from about 1 nanometer to about 25 nm.

In some embodiments, the hollow fiber membrane may include a blend of a block copolymer described earlier with at least one additional polymer. The additional polymer may be blended with the block copolymer to impart different properties such as better heat resistance, biocompatibility, and the like. Furthermore, the additional polymer may be added to the block copolymer during the membrane formation to modify the morphology of the phase inverted membrane structure produced upon phase inversion, such as asymmetric membrane structures. In addition, at least one polymer that is blended with the block copolymer may be hydrophilic or hydrophobic in nature.

In some embodiments, the block copolymer is blended with a hydrophilic polymer. Non-limiting example of a suitable hydrophilic polymer includes polyvinylpyrrolidone (PVP). Non-limiting examples of other suitable hydrophilic polymers include polyoxazoline, polyethyleneglycol, polypropylene glycol, polyglycolmonoester, copolymer of polyethyleneglycol with polypropylene glycol, water-soluble cellulose derivative, polysorbate, polyethylene-polypropylene oxide copolymer, polyethyleneimine, and combinations thereof. In some embodiments, the block copolymer may be further blended with polymers, such as, polysulfone, polyether sulfone, polyether urethane, polyamide, polyetheramide, polyacrylonitrile, and combinations thereof.

The membranes in accordance with some embodiments of the invention may have use in various applications, such as, bio-separation, water purification, hemofiltration, hemodialysis, ultrafiltration, nanofiltration, gas separation, microfiltration, reverse osmosis, and pervaporation. In particular embodiments, the membranes may have applications in the biopharmaceutical and biomedical field where improved hydrophilicity and biocompatibility are desired.

In some embodiments, a hollow-fiber membrane for bio-separation is presented. A hollow-fiber membrane suitable for bio-separation may be characterized in part by the protein binding. In some embodiments, the hollow-fiber membranes may have protein binding less than about 30 ng/cm$^2$. The membrane is composed of a block copolymer in accordance with embodiments of the invention. In another aspect, the present invention relates to a bio-separation apparatus that includes a plurality of porous hollow fibers composed of the porous membranes of the present invention.

In some embodiments, the membranes in accordance with some embodiments of the invention may be used for hemodialysis. Dialysis refers to a process effected by one or more membranes in which transport is driven primarily by pressure differences across the thickness of the one or more membrane. Hemodialysis refers to a dialysis process in which biologically undesired and/or toxic solutes, such as metabolites and by-products are removed from blood. Hemodialysis membranes are porous membranes permitting the passage of low molecular weight solutes, typically less than 5,000 Daltons, such as urea, creatinine, uric acid, electrolytes and water, yet preventing the passage of higher molecular weight proteins and blood cellular elements. Hemofiltration, which more closely represents the filtration in the glomerulus of the kidney, requires even more permeable membranes allowing complete passage of solutes of molecular weight of less than 50,000 Daltons, and, in some cases, less than 20,000 Daltons Without being bound by any theory it is believed that the block copolymer in accordance with some embodiments of the present invention have the desired mechanical properties so as to support the porous membrane structure during manufacture and use. In addition, the block copolymer has adequate thermal properties so as not to degrade during high temperature steam sterilization processes. Further, the block copolymer and the corresponding membranes have optimal biocompatibility, such that protein fouling is minimized and thrombosis of the treated blood does not occur.

EXAMPLES

Chemicals were purchased from Aldrich and Sloss Industries and used as received, unless otherwise noted. NMR spectra were recorded on a Bruker Avance 400 ($^1$H, 400 MHz) spectrometer and referenced versus residual solvent shifts. Molecular weights are reported as number average ($M_n$) or weight average ($M_w$) molecular weight and were determined by gel permeation chromatography (GPC) analysis on a Perkin Elmer Series 200 instrument equipped with UV detector. Polymer thermal analysis was performed on a Perkin Elmer DSC7 equipped with a TACT/DX thermal analyzer and processed using Pyris Software.

Glass transition temperatures were recorded on the second heating scan. Contact angle measurements were taken on a VCA 2000 (Advanced Surface Technology, Inc.) instrument using VCA optima Software for evaluation. Polymer films were obtained from casting a thin film from an appropriate solution, such as, dimethyl sulfoxide (DMSO), N-methyl-2-pyrrolidone (NMP), and dimethylacetamide (DMAC) onto a clean glass slide and evaporation of the solvent. Advancing contact angles with water (73 Dynes/cm) were determined on both sides of the film (facing air and facing glass slide). Consistently lower values were obtained on the side facing the glass slide presumably due to the smoother surface.

Example 1

Synthesis of End-Capped Polysulfone Macroinitiator Br-PSUx-Br

The synthetic scheme for synthesis Br-PSUx-Br is shown in FIG. 1. It should be noted that "Br-PSUx-Br" refers to Br-end capped PSU polymer and further includes linking groups as shown in scheme 1. A 50-L glass-lined reactor was first charged with 9.0 L of NMP at room temperature (RT). 1 kg bisphenol-A (BPA) (4.38 mol, MW=228.29 g/mol) and 1 kg $K_2CO_3$ (7.23 mol) were then added to the reactor. The mixture was stirred slowly to ensure complete dissolution of the Bisphenol-A, and then 2.5 L toluene was charged to the reactor equipped with mechanical stirrer, Dean Stark trap, and nitrogen purge capabilities. The mixture was then heated to 125° C. (thermocouple temperature in reactor) with nitrogen purge at about 1 scfh (standard cubic feet per hour), while stirring at 200 rpm. At 125° C., water was removed azeotropically over the course of 3 hours with occasional addition of toluene (2×1 L).

When all of the water was removed azeotropically, then the reaction was cooled overnight to RT. 1.24 kg 4,4'-dichlorodiphenylsulfone (DCDPS) (4.3 mol, MW=287.16 g/mol) was then added to the reaction mixture. Toluene (2×1 L) was further added to remove additional water. The mixture was stirred at 170° C. for about 8 hours, at which point a highly viscous solution was formed. The viscous mixture was diluted with 9 L NMP, cooled to room temperature, and allowed to stir overnight. 3 L light brown polymer solution was added to 30 L of excess water to precipitate the polymer in a Henschel Homogenizer. The polymer was collected via centrifugation and successively washed with water, and then methanol. The polymer was then dried in vacuum to remove residual solvent.

The dried polymer was then dissolved in 12 L methylene chloride. 45.0 g triethylamine (0.445 mol) and 100 g of 2-bromoisobutyryl bromide (0.435 mol) were added slowly and sequentially. The reaction mixture was stirred overnight at RT, and the 6 L light brown polymer solution was then precipitated into 30 L methanol using a Henschel Homogenizer. The polymer was soaked in water for 2 days to remove any residual salts, filtered via centrifugation, and then washed with methanol. 1.75 kg (91% yield) Br-PSU$_{75}$-Br was produced which was further dried in vacuum at 50° C. overnight to remove residual solvents. GPC (UV detector) with $CHCl_3$ showed a final $M_w$ of 46,000 and $M_n$ of 27,500 g/mol.

Similarly, two other macroinitiators: Br-PSU$_{52}$-Br and Br-PSU$_{50}$-Br were also prepared using the above synthetic scheme and procedure.

Example 2

Synthesis of End-Capped Polysulfone Macroinitiator Br-PSUx

Figure 2:
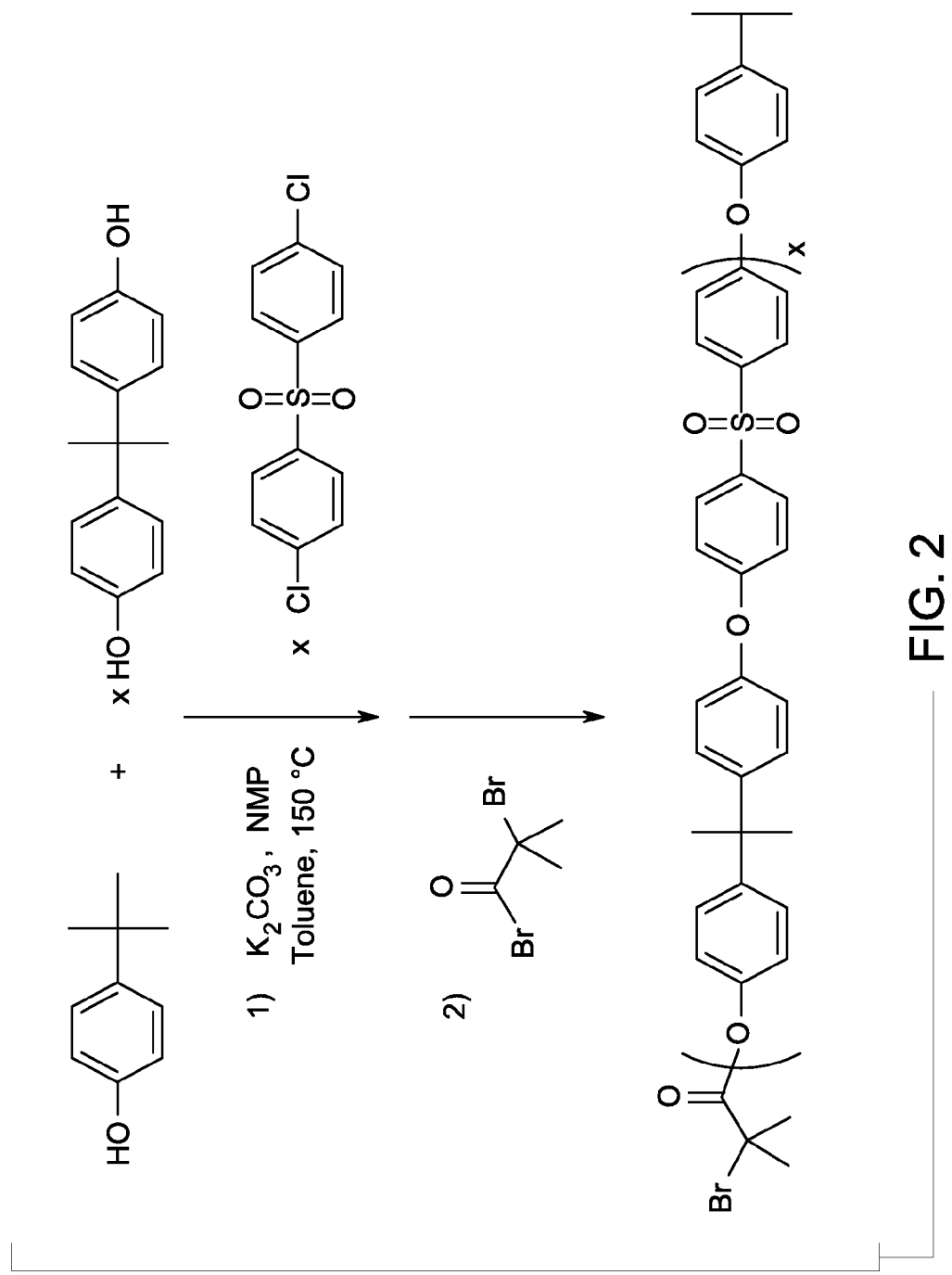
FIG. 2 shows the synthesis scheme for the macroinitiator, in accordance with some embodiments of the invention.

The synthetic scheme for synthesis of Br-PSUx is shown in FIG. 2. A phenolic endcapping agent, 4-tert-butylphenol, was utilized to react with the free fluorophenylsulfone (or chlorophenylsulfone) end group, and thereby producing an ATRP-active end-capped polysulfone comprising only one active site. Bisphenol-A and 4-tert-butylphenol were reacted with dichlorodiphenylsulfone (DCDPS) in the presence of base to give the hydroxide-functionalized polysulfone, which was subsequently reacted with 2-bromoisobutyryl bromides. The reaction was successfully completed giving 97% yield and produced 6.5 kilograms of the end-capped polysulfone Br-PSU$_{50}$.

Example 3

Synthesis of P(DMAEMA)$_y$-PSU$_x$-P(DMAEMA)$_y$ block copolymer

Figure 3:
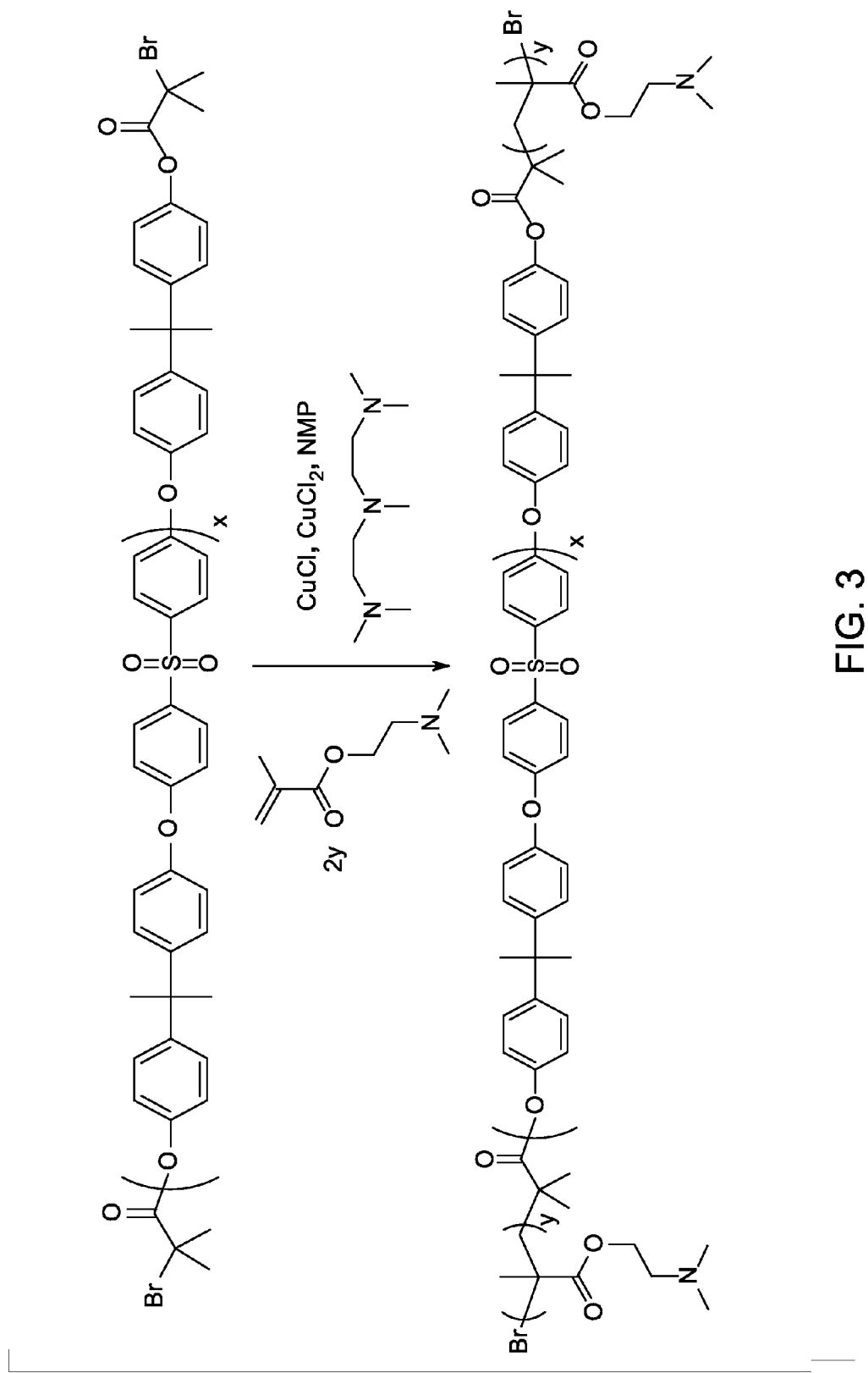
FIG. 3 shows the synthesis scheme for the block copolymer, in accordance with some embodiments of the invention.

The synthetic scheme for synthesis of block copolymer is shown in FIG. 3.

Synthesis of (DMAEMA)$_{11.4}$-PSU$_{75}$-P(DMAEMA)$_{11.4}$: 4.0 g Br-PSU$_{75}$-Br (0.35 mmol of Br initiator) was dissolved in 16.0 mL NMP in an oven-dried Schlenk tube equipped with a magnetic stir bar. The viscous solution was cooled to room temperature, and 1.106 g DMAEMA (N,N-dimethylaminoethyl methacrylate, 7.03 mmol) and 0.15 mL PMDETA (pentamethyldiethylenetriamine, 0.72 mmol) were added. Three freeze-pump-thaw cycles were performed to remove dissolved gases. The Schlenk tube was backfilled with nitrogen and 20.0 mg copper (I) chloride (0.20 mmol) and 12.8 mg copper (II) chloride (0.095 mmol) were added under a nitrogen purge. The contents were warmed to 40° C., and the greenish-brown solution was stirred for 16 hours. The reaction was diluted with 16 mL tetrahydrofuran and ~5 g basic alumina was added to bind copper ions. The mixture was filtered over a bed of celite and basic alumina. 200 mL water was added to precipitate the polymer. The off-white solid was collected by filtration, washed with water and then with methanol, and then dried in vacuo at 50° C. overnight to remove residual solvent.

Similarly, four other block copolymers: $(DMAEMA)_{6.5}$-$PSU_{52}$-$P(DMAEMA)_{6.5}$; $(DMAEMA)_{3.5}$-$PSU_{52}$-$P(DMAEMA)_{3.5}$; $(DMAEMA)_{3.0}$-$PSU_{52}$-$P(DMAEMA)_{3.0}$; and $(DMAEMA)_{20}$-$PSU_{50}$ were also synthesized using the above synthetic scheme and procedure.

Example 4

Synthesis of Zwitterion-Functionalized Block Copolymers

The block copolymers synthesized in Example 3 and 1,3 propane sultone were dissolved in 15 ml of NMP. The solution was heated to 80° Compressor 100 to afford a solid. The solid was broken apart in a blender. The resulting powder was filtered and dried in vacuo. The mole fraction of zwitterion functional groups in the block copolymers was controlled by reacting the block copolymers with the corresponding amount of sultone. Table 1 provides the details of the block copolymer compositions.

TABLE 1

Composition details of zwitterion-functionalized block copolymers

| Sample No. | Copolymer Type | Block length (y-x-y) | % Acrylate functionalized with sultone |
|---|---|---|---|
| 1 | $A_y$-$B_x$-$A_y$ | 11.4-75-11.4 | 35% |
| 2 | $A_y$-$B_x$-$A_y$ | 11.4-75-11.4 | 70% |
| 3 | $A_y$-$B_x$-$A_y$ | 11.4-75-11.4 | 50% |
| 4 | $A_y$-$B_x$-$A_y$ | 6.5-52-6.5 | 100% |
| 5 | $A_y$-$B_x$-$A_y$ | 6.5-52-6.5 | 50% |
| 6 | $A_y$-$B_x$-$A_y$ | 3.5-52-3.5 | 100% |
| 7 | $A_y$-$B_x$-$A_y$ | 20-50 | 50% |
| 8 | $A_y$-$B_x$ | 3.0-52-3.0 | 100% |

Example 5

Protein Adhesion Studies

Films cast using zwitterion-functionalized block copolymers (samples 1 and 3) were evaluated for protein binding. Hollow fiber porous membranes were prepared from sample 8 and evaluated for protein binding.

Dense films were blocked so that only the top surface (that which was exposed to air when the film was cast) was exposed to the model foulant, an HRP-labeled antibody. The surfaces were covered with a 10 µg/ml solution of HRP-Ab for 2 hours and washed thoroughly with PBS for another hour to remove loosely-adhered Ab. Using a 0.5 cm diameter biopsy punch, disks were cut from the film and 3 disks from each polymer film were transferred individually to a 24-well plate. To each well was added 0.5 ml of a solution of o-phenylene diamine, hydrogen peroxide, and citrate phosphate buffer (0.5 mg/ml, 0.015%, and 50 mM, respectively). Exactly three minutes after this solution was added, the absorbance of the solution was measured at 450 nm. The HRP enzyme on the antibody converts the o-phenylene diamine to a colored product, and thus the absorbance of the solution can be correlated to the amount of antibody that has fouled the surface of the dense film using a calibration curve. When this method is used to determine the fouling on hollow fibers, 1-inch long pieces of hollow fiber are submerged in the antibody solution for 2 hours, washed thoroughly with PBS for an additional hour, cut into quarters and the 4 quarters are transferred collectively to the wells of a 24-well plate. The enzymatic reaction and spectrophotometry are carried out as described above. Inner and outer diameter of each fiber were measured microscopically and used to calculate nominal surface area of the sample. Surface coverage was normalized by surface area.

Figure 4:
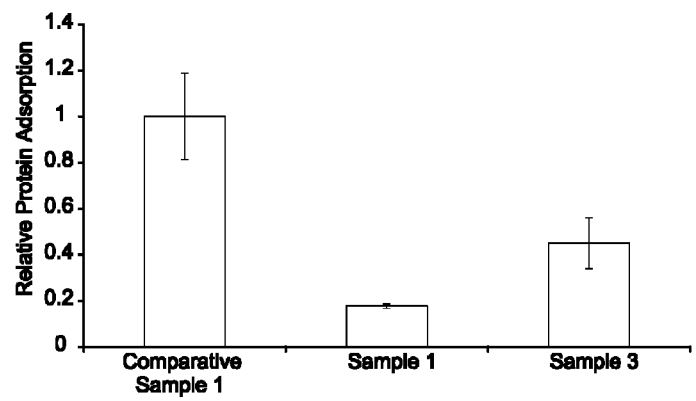
FIG. 4 shows the normalized protein adhesion values for comparative sample and for block copolymer films, in accordance with some embodiments of the invention.
Figure 5:
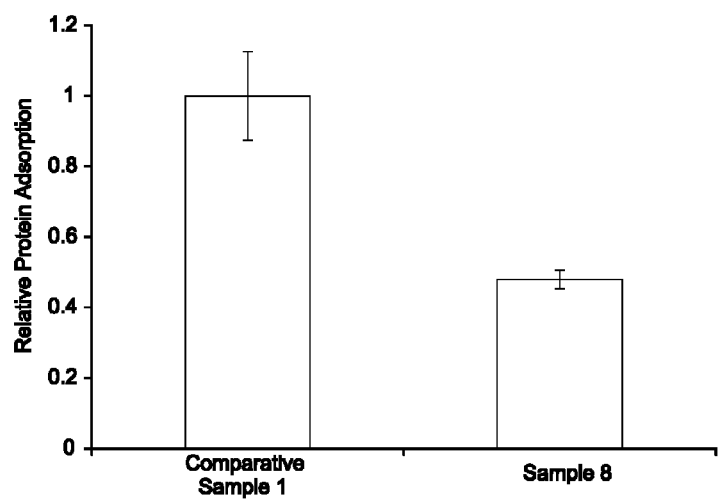
FIG. 5 shows the normalized protein adhesion values for comparative sample and for block copolymer hollow fiber membrane, in accordance with some embodiments of the invention.

FIG. 4 shows the normalized protein binding performance (normalized with respect to PSU) for commercial polysulfone (PSU) (comparative example 1) versus films cast using samples 1 and 3. FIG. 5 shows the normalized protein binding performance (normalized with respect to PSU) for commercial polysulfone (comparative example 1) versus hollow-fiber membrane formed using sample 8.

As illustrated in FIGS. 4 and 5, copolymers with the zwitterion groups provide improved performance versus commercial polysulfone (PSU). The improved protein adhesion performance may be attributed to the presence of the zwitterion group in the copolymer. Further, it was shown that the zwitterion group in the copolymer does not inhibit the ability of the copolymer to make hydrophilic hollow fiber membranes with useful porosities and mechanical performance for commercial hollow fiber applications. Furthermore, the block copolymers in accordance with some embodiments of the invention showed unexpectedly good performance versus piperazine functionalized polysulfone, considering that the zwitterion content in the block copolymers in accordance with some embodiments of the invention was lower when compared to the piperazine functionalized polysulfone.

The appended claims are intended to claim the invention as broadly as it has been conceived and the examples herein presented are illustrative of selected embodiments from a manifold of all possible embodiments. Accordingly, it is the Applicants' intention that the appended claims are not to be limited by the choice of examples utilized to illustrate features of the present invention. As used in the claims, the word "comprises" and its grammatical variants logically also subtend and include phrases of varying and differing extent such as for example, but not limited thereto, "consisting essentially of" and "consisting of." Where necessary, ranges have been supplied; those ranges are inclusive of all sub-ranges there between. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims.

The invention claimed is:
1. A membrane, comprising:
a block copolymer comprising at least one block A comprising structural units having a formula (I), and at least one block B comprising structural units having a formula (II):

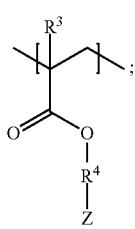
(I)

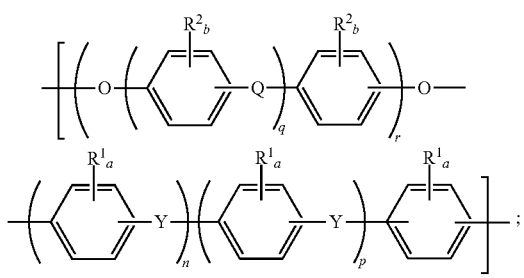
(II)

wherein "a" and "b" are independently at each occurrence 0, 1, 2, 3, or 4;
"n", "p", "q" and "r" are independently 0 or 1;
R1 and R2 are independently at each occurrence a hydrogen atom, a nitro group, a C1-C12 aliphatic radical, a C3-C12 cycloaliphatic radical, or a C3-C12 aromatic radical;
R3 is a hydrogen atom, a C1-C12 aliphatic radical, a C3-C12 cycloaliphatic radical, or a C3-C12 aromatic radical;
R4 is a C1-C12 aliphatic radical, a C3-C12 cycloaliphatic radical, or a C3-C12 aromatic radical;
Y is independently at each occurrence a bond, an oxygen atom, a sulfur atom, a sulfinyl group, a sulfonyl group, a phenylphosphine group, a C1-C12 aliphatic radical, a C3-C12 cycloaliphatic radical, or a C3-C12 aromatic radical;
Q is a bond, an oxygen atom, a sulfur atom, a C1-C12 aliphatic radical, a C3-C12 cycloaliphatic radical, or a C3-C12 aromatic radical; and
Z is a zwitterion functional group.
2. The membrane of claim 1, wherein the block B comprises structural units having a formula (III):

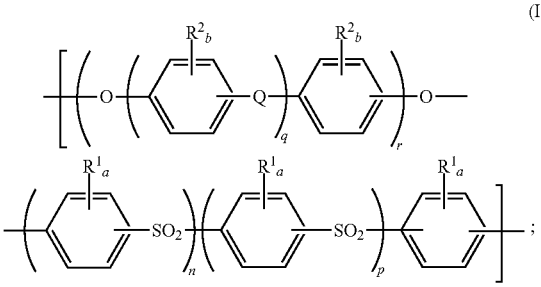
(III)

wherein "a" and "b" are independently at each occurrence 0, 1, 2, 3, or 4;
"n", "p", "q" and "r" are independently 0 or 1;
Q is a bond, an oxygen atom, a sulfur atom, a C1-C12 aliphatic radical, a C3-C12 cycloaliphatic radical, or a C3-C12 aromatic radical; and
R1 and R2 are independently at each occurrence a hydrogen atom, a nitro group, a C1-C12 aliphatic radical, a C3-C12 cycloaliphatic radical, or a C3-C12 aromatic radical.
3. The membrane of claim 1, wherein the zwitterion functional group comprises sulfobetaine, carboxybetaine, phosphorylcholine, or combinations thereof.
4. The membrane of claim 1, wherein the block A comprises structural units having a formula (IV):

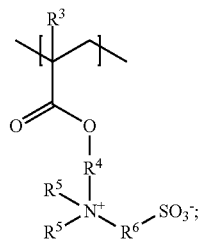
(IV)

wherein $R^3$ and $R^5$ are independently at each occurrence a hydrogen atom, a $C_1$-$C_{12}$ aliphatic radical, a $C_3$-$C_{12}$ cycloaliphatic radical, or a $C_3$-$C_{12}$ aromatic radical; and
$R^4$ and $R^6$ are independently a $C_1$-$C_{12}$ aliphatic radical, a $C_3$-$C_{12}$ cycloaliphatic radical, or a $C_3$-$C_{12}$ aromatic radical.
5. The membrane of claim 1, wherein the block A further comprises structural units having a formula (V):

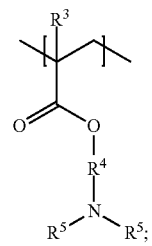
(V)

$R^3$ and $R^5$ are independently at each occurrence a hydrogen atom, a $C_1$-$C_{12}$ aliphatic radical, a $C_3$-$C_{12}$ cycloaliphatic radical, or a $C_3$-$C_{12}$ aromatic radical; and
$R^4$ is a $C_1$-$C_{12}$ aliphatic radical, a $C_3$-$C_{12}$ cycloaliphatic radical, or a $C_3$-$C_{12}$ aromatic radical.
6. The membrane of claim 1, wherein a mole fraction of the zwitterion functional group in the block A is in a range from about about 5 percent to about 100 percent.
7. The membrane of claim 1, wherein a mole fraction of the zwitterion functional group in the block A is in a range from about about 35 percent to about 70 percent.
8. The membrane of claim 1, wherein the number of repeat units in the block B is in a range from about 20 to about 200.
9. The membrane of claim 1, wherein the number of repeat units in the block A is in a range from about 1 to about 25.

10. The membrane of claim 1, wherein the block copolymer comprises structural units having a formula (VI):

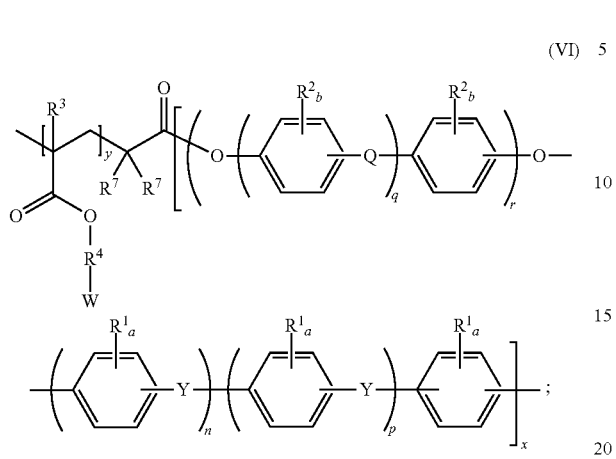

(VI)

wherein "a" and "b" are independently at each occurrence 0, 1, 2, 3, or 4;

"n", "p", "q" and "r" are independently 0 or 1;

"x" is an integer in a range from about 20 to about 200;

"y" is an integer in a range from about 1 to about 25;

Y is independently at each occurrence a bond, an oxygen atom, a sulfur atom, a sulfinyl group, a sulfonyl group, a phenylphosphine group, a $C_1$-$C_{12}$ aliphatic radical, a $C_3$-$C_{12}$ cycloaliphatic radical, or a $C_3$-$C_{12}$ aromatic radical;

Q is a bond, an oxygen atom, a sulfur atom, a $C_1$-$C_{12}$ aliphatic radical, a $C_3$-$C_{12}$ cycloaliphatic radical, or a $C_3$-$C_{12}$ aromatic radical;

W is independently at each occurrence a radical having a formula (VII) or (VIII):

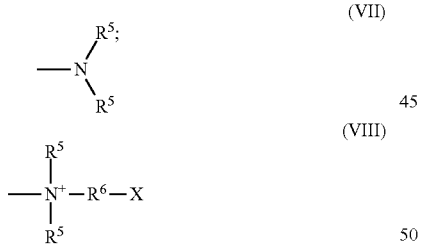

(VII)

(VIII)

with the proviso that at least one of W in the block copolymer is a radical having the formula (VIII);

$R^1$ and $R^2$ are independently at each occurrence a hydrogen atom, a nitro group, a $C_1$-$C_{12}$ aliphatic radical, a $C_3$-$C_{12}$ cycloaliphatic radical, or a $C_3$-$C_{12}$ aromatic radical;

$R^3$, $R^5$, and $R^7$ are independently at each occurrence a hydrogen atom, a $C_1$-$C_{12}$ aliphatic radical, a $C_3$-$C_{12}$ cycloaliphatic radical, or a $C_3$-$C_{12}$ aromatic radical; and $R^4$ and $R^6$ are independently a $C_1$-$C_{12}$ aliphatic radical, a $C_3$-$C_{12}$ cycloaliphatic radical, or a $C_3$-$C_{12}$ aromatic radical.

11. The membrane of claim 1, wherein the block copolymer comprises structural units having a formula (IX):

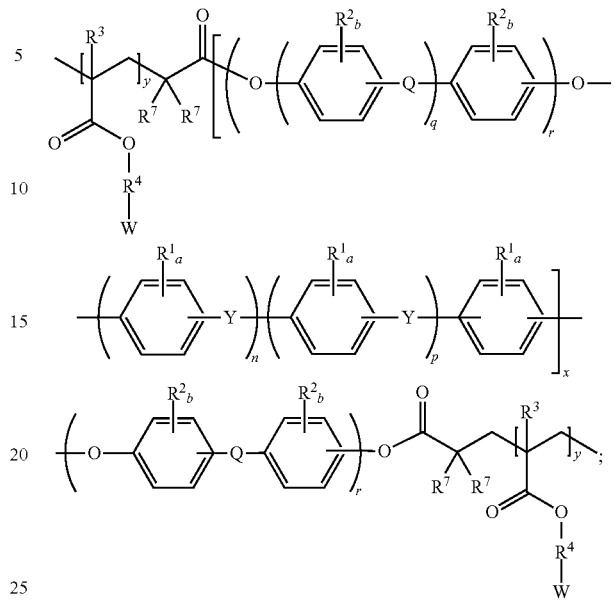

(IX)

wherein "a" and "b" are independently at each occurrence 0, 1, 2, 3, or 4;

"n", "p", "q" and "r" are independently 0 or 1;

"x" is an integer in a range from about 20 to about 200;

"y" is an integer in a range from about 1 to about 25;

Y is independently at each occurrence a bond, an oxygen atom, a sulfur atom, a sulfinyl group, a sulfonyl group, a phenylphosphine group, a $C_1$-$C_{12}$ aliphatic radical, a $C_3$-$C_{12}$ cycloaliphatic radical, or a $C_3$-$C_{12}$ aromatic radical;

Q is a bond, an oxygen atom, a sulfur atom, a $C_1$-$C_{12}$ aliphatic radical, a $C_3$-$C_{12}$ cycloaliphatic radical, or a $C_3$-$C_{12}$ aromatic radical;

W is independently at each occurrence a radical having a formula (VII) or (VIII):

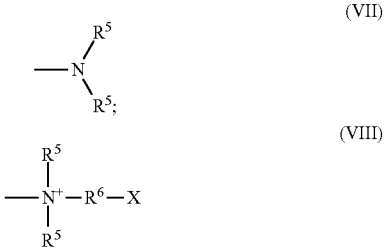

(VII)

(VIII)

with the proviso that at least one W in the block copolymer is a radical having the formula (VIII);

$R^1$ and $R^2$ are independently at each occurrence a hydrogen atom, a nitro group, a $C_1$-$C_{12}$ aliphatic radical, a $C_3$-$C_{12}$ cycloaliphatic radical, or a $C_3$-$C_{12}$ aromatic radical;

$R^3$, $R^5$, and $R^7$ are independently at each occurrence a hydrogen atom, a $C_1$-$C_{12}$ aliphatic radical, a $C_3$-$C_{12}$ cycloaliphatic radical, or a $C_3$-$C_{12}$ aromatic radical; and $R^4$ and $R^6$ are independently a $C_1$-$C_{12}$ aliphatic radical, a $C_3$-$C_{12}$ cycloaliphatic radical, or a $C_3$-$C_{12}$ aromatic radical.

12. The membrane of claim 1, wherein the membrane has a hollow-fiber configuration.

13. A hollow-fiber module comprising a plurality of membranes as defined in claim 11.

14. A hollow-fiber membrane for bio-separation, comprising a block copolymer comprising at least one block A comprising structural units having a formula (I), and at least one block B comprising structural units having a formula (II):

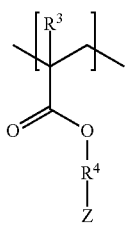
(I)

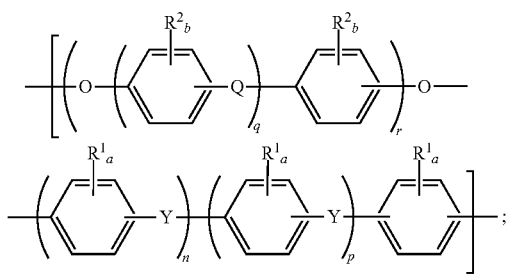
(II)

wherein "a" and "b" are independently at each occurrence 0, 1, 2, 3, or 4;

"n", "p", "q" and "r" are independently 0 or 1;

R1 and R2 are independently at each occurrence a hydrogen atom, a nitro group, a C1-C12 aliphatic radical, a C3-C12 cycloaliphatic radical, or a C3-C12 aromatic radical;

R3 is a hydrogen atom, a C1-C12 aliphatic radical, a C3-C12 cycloaliphatic radical, or a C3-C12 aromatic radical;

R4 is a C1-C12 aliphatic radical, a C3-C12 cycloaliphatic radical, or a C3-C12 aromatic radical;

Y is independently at each occurrence a bond, an oxygen atom, a sulfur atom, a sulfinyl group, a sulfonyl group, a phenylphosphine group, a C1-C12 aliphatic radical, a C3-C12 cycloaliphatic radical, or a C3-C12 aromatic radical;

Q is a bond, an oxygen atom, a sulfur atom, a $C_1$-$C_{12}$ aliphatic radical, a $C_3$-$C_{12}$ cycloaliphatic radical, or a $C_3$-$C_{12}$ aromatic radical; and Z is a zwitterion functional group.

15. The hollow-fiber membrane of claim 14, wherein the block B comprises structural units having a formula (III)

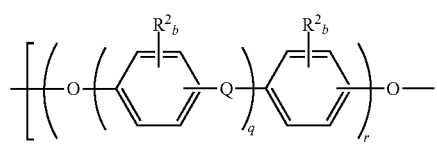
(III)

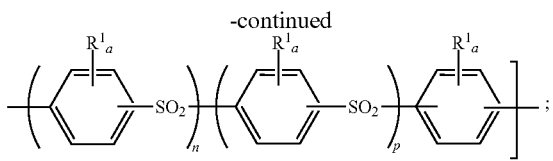

wherein "a" and "b" are independently at each occurrence 0, 1, 2, 3, or 4;

"n", "p", "q" and "r" are independently 0 or 1;

Q is a bond, an oxygen atom, a sulfur atom, a C1-C12 aliphatic radical, a C3-C12 cycloaliphatic radical, or a C3-C12 aromatic radical; and R1 and R2 are independently at each occurrence a hydrogen atom, a nitro group, a C1-C12 aliphatic radical, a C3-C12 cycloaliphatic radical, or a C3-C12 aromatic radical.

16. The hollow-fiber membrane of claim 14, wherein the zwitterion functional group comprises sulfobetaine, carboxybetaine, phosphorylcholine, or combinations thereof.

17. The hollow-fiber membrane of claim 14, wherein the block A comprises structural units having a formula (IV):

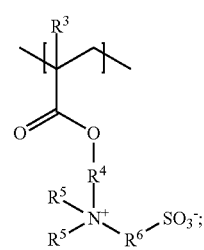
(IV)

wherein $R^3$ and $R^5$ are independently at each occurrence a hydrogen atom, a $C_1$-$C_{12}$ aliphatic radical, a $C_3$-$C_{12}$ cycloaliphatic radical, or a $C_3$-$C_{12}$ aromatic radical; and $R^4$ and $R^6$ are independently a $C_1$-$C_{12}$ aliphatic radical, a $C_3$-$C_{12}$ cycloaliphatic radical, or a $C_3$-$C_{12}$ aromatic radical.

18. The hollow-fiber membrane of claim 14, wherein the block A further comprises structural units having a formula (V):

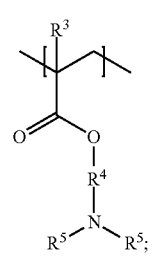
(V)

R3 and R5 are independently at each occurrence a hydrogen atom, a C1-C12 aliphatic radical, a C3-C12 cycloaliphatic radical, or a C3-C12 aromatic radical; and R4 is a C1-C12 aliphatic radical, a C3-C12 cycloaliphatic radical, or a C3-C12 aromatic radical.

* * * * *